United States Patent [19]

Camp et al.

[11] Patent Number: 5,043,090

[45] Date of Patent: Aug. 27, 1991

[54] METHOD FOR MANUFACTURING TOILET BOWL CLEANERS CONTAINING IODOPHORS

[75] Inventors: William R. Camp, Reading; Charles J. Bunczk, Norristown; Peter A. Burke, Downingtown, all of Pa.

[73] Assignee: Kiwi Brands, Inc., Douglassville, Pa.

[21] Appl. No.: 488,889

[22] Filed: Mar. 5, 1990

[51] Int. Cl.[5] .......... C11D 3/48; A01N 59/12; A61K 33/18

[52] U.S. Cl. .......... 252/106; 23/313 R; 23/313 P; 424/672

[58] Field of Search .......... 252/106; 23/313 R, 313 P; 424/672

[56] References Cited

U.S. PATENT DOCUMENTS

| | | | |
|---|---|---|---|
| 2,743,208 | 4/1956 | Marcuse et al. | 426/672 |
| 4,722,801 | 2/1988 | Bunczk et al. | 252/106 |
| 4,725,434 | 2/1988 | Jauw | 426/672 |
| 4,844,899 | 7/1989 | Juda et al. | 424/644 |
| 4,894,241 | 1/1990 | Chakrabarti et al. | 424/672 |

OTHER PUBLICATIONS

Browning, Joe E. "Agglomeration Growing Larger in Applications and Technology," Chemical Engineering, Dec. 4, 1967, pp. 147-169.

*Primary Examiner*—Paul Lieberman
*Assistant Examiner*—Cynthia Leslie
*Attorney, Agent, or Firm*—John Lezdey

[57] ABSTRACT

The invention is a process for manufacturing an iodophor filler for a lavatory cleaning cake. The process involves mixing in a dry-mixer means or "Turbulizer" a dry filler composition. The dry filler composition contains an adsorbent and the dry-mixer means provides a uniform turbulent flow of the dry filler composition as the composition passes through the dry-mixer means. The method then involves wetting the dry filler composition with a liquid iodophor while the composition is in the uniform turbulent flow. Agglomerating of the wetted filler composition then occurs within a controlled residence time of the wetted filler composition in the dry-mixer means whereby the iodophor is substantially uniformly distributed throughout the dry filler composition. The dry filler composition, desirably, includes both a dry adsorbent and a dry absorbent. This invention includes the product of the process.

28 Claims, 3 Drawing Sheets

METHOD FOR MANUFACTURING TOILET BOWL CLEANERS CONTAINING IODOPHORS

This is application relates to U.S. patent application Ser. No. 426,793, filed Oct. 26, 1989, which is incorporated herein by reference.

BACKGROUND OF THE INVENTION

1. Field of the Invention

The present invention relates to a method for manufacturing a cake composition which is useful for the treatment of the flush water of toilets. More particularly, the invention relates to a method for manufacturing a cake composition with a long lasting iodophor-containing toilet tank dispenser which provides improved cleaning, a sanitizing action and is responsive to the flushing of the toilet.

2. Background Art of the Invention

It is desirable that chemicals be automatically dispensed into toilet flush water each time a toilet is flushed in order to produce desirable bowl aesthetics, cleaning, disinfection, deodorization, aerosol reduction, or other desirable effects. The background art discloses numerous devices which are designed for one or more of these purposes.

Particularly desirable devices are those comprising a solid cake composition. A measured amount of water, in this type of device, enters the device during one flush cycle and remains in contact with the cake between flushes, thereby forming a concentrated solution of the composition. The concentrated solution of the composition is then dispensed into the flush water during the next flush. The advantages of such devices are that the chemical composition can be packaged and shipped in more concentrated form than aqueous solutions of the chemicals. Also, there is no problem with liquid spillage, that can result from breakage of the dispensers during shipment or handling.

U.S. Pat. No. 4,780,236 to Bunczk, et al., issued Oct. 25, 1988, herein incorporated by reference, discloses a lavatory cleansing block containing polyethylene glycol distearate, guar gum, and sodium chloride. This patent, particularly in columns 3 through 5, identifies a variety of compositions and their concentrations for use in manufacturing a lavatory cleansing block or "toilet cake". This patent does not disclose a method for manufacturing such a block with a dye and iodophor composition that release from the block during substantially the same period of time.

U.S. Pat. Nos. 4,308,625 to Kitko, issued Jan. 5, 1982, and 4,043,931 to Jeffrey, et al., issued Aug. 23, 1977, are examples of surfactant cake compositions. These patents disclose lavatory cleansing tablets which are formed with two or more nonionic surfactants and which include the use of polyalkoxylated alcohols.

U.S. Pat. No. 4,477,363 to Wong, et al., issued Oct. 16, 1984, discloses a solid cake comprising free fatty alcohol and a buffered alkali earth metal alkyl sulfate surfactant.

U.S. Pat. Nos. 4,310,434 Choy, et al., issued Jan. 12, 1982, and 4,278,571 to Choy, issued July 14, 1981, are entitled "Surfactant Cake Compositions" and are both incorporated herein by reference. These two patents disclose surfactant cake compositions containing dyes and perfumes which can be utilized in the present invention. The surfactants provide cleaning and sudsing activity in the toilet bowl and also serve to dispense other components of the compositions such as dyes, perfumes, and organic resins into the toilet water.

Water-soluble inert salts such as alkali metal chlorides and sulfates are used in such compositions to act as a "filler" so that the composition can be formed into cakes of desirable size without using excessive amounts of active ingredients. The predominant ingredients of the cake compositions are usually the surfactant, perfume, and the filler salt.

Automatically dispensed toilet bowl cleaning and/or sanitizing products, which contain dyes to provide a visual signal to the user that the product is being dispensed, are well known. Such products are sold in the United States under the brand names VANISH AUTOMATIC (Drackett Products), TY-D-BOL AUTOMATIC (Kiwi Brands, Inc.) and SANIFLUSH AUTOMATIC (Boyle-Midway). None of these products contain an iodophor sanitizing agent and all of them provide a color to the bowl water which persists between flushings. U.S. Pat. No. 3,504,384 to Radley et al., issued Apr. 7, 1970, discloses a dual compartment dispenser for automatically dispensing a hypochlorite solution and a surfactant/dye solution to the toilet bowl during flushing. The dye which is taught in the patent is Disulfide Blue VN150. This dye is resistant to oxidation to a colorless state by the hypochlorite. Thus, the dye provides a persistent color to the toilet bowl water, even in the presence of the hypochlorite.

The Environmental Protection Agency has established efficacy data requirements for in-tank sanitizer product claims for effectiveness. It is necessary under these requirements that the user be able to determine the duration of the product's effectiveness. That is, the color indicator of the product must show that the sanitizing ingredient is still present in a sanitizing amount or guarantee a specific life or number of flushes. Consequently, it is essential that the sanitizing agent have the same life in the sanitizing product as the color indicator.

The use of chlorine or hypochlorite ion as the sanitizing agent has the disadvantage that most dyes are oxidized to a colorless state by these compounds and there is no visual indication that the sanitizing agent is active and working in the toilet bowl.

The use of iodine-containing formulations have been previously considered as sanitizing agents for toilets because of their greater sanitizing capabilities than the sanitizing capabilities of chlorine-containing agents. However, the iodine-containing agents have not been previously employed in cake toilet compositions because they yield an unacceptable color in the toilet bowl. Also, prior to the present invention, there has not been a means for providing a controlled release of iodine so that the iodine and the dye will last for the life of the cleansing block. The most effective means to date for such products provides the iodine in a germicidal complex of iodine with a copolymer. These iodine complexes are commonly identified as an iodophor.

It is an object of the present invention to provide a method for manufacturing a solid cake, containing iodophors, which is suitable for use for automatically dispensing cleaning agents into a toilet.

It is another object of the present invention to provide a method for manufacturing a filler for a lavatory block which has a uniform distribution of iodophor throughout an adsorbent-containing dry filler composition.

It is still a further object of the present invention to provide a method for manufacturing a lavatory block having a long and uniform block life that provides a controlled release of iodophor.

It is a yet still further object of the present invention to provide a method for manufacturing an iodophor-containing lavatory block which releases a dye and an iodophor for substantially the same period of time.

Other objects, advantages, and novel features of the present invention will be apparent to those skilled in the art from the following description and appended claims.

SUMMARY OF THE INVENTION

The objectives of the invention are achieved by a process for manufacturing an iodophor filler for a lavatory cleaning cake. This process involves mixing in a dry-mixer means a dry filler composition containing an adsorbent. The dry-mixer means provides a uniform turbulent flow of the dry filler composition through the dry-mixer means. The process then involves wetting the dry filler composition in the uniform turbulent flow with a liquid iodophor whereby the iodophor is substantially, uniformly distributed throughout the filler composition. Then, agglomerating of the wetted filler composition occurs within a controlled residence time of the wetted filler composition in the dry-mixer means. The process may be continuous or batchwise.

This invention further includes a process for manufacturing an iodophor lavatory cleaning cake. A desirable embodiment of this process involves blending a dry adsorbent and a dry absorbent to produce a filler composition. The filler composition then undergoes mixing in a dry-mixer means which provides a uniform turbulent flow of the filler composition through the dry-mixer means. Wetting of the dry filler composition then occurs in the uniform turbulent flow with a liquid iodophor whereby the iodophor is substantially, uniformly distributed throughout the filler composition. Agglomerating of the wetted filler composition occurs within a controlled residence time within which the wetted filler composition is in the dry-mixer means. The process then involves blending a sufficient quantity of a dye into the agglomerated filler composition and compressing the dye-containing filler composition into a solid. Lastly, compressing of the agglomerated filler composition into a solid form occurs whereby, when the solid form is immersed in an aqueous solution, the sufficient quantity of the dye releases into solution for a time substantially equivalent to a release of the iodophor into solution from the solid form.

The invention includes the product of the process which is an iodophor filler or an iodophor-containing laboratory cleaning cake wherein the iodophor is substantially, uniformly mixed throughout the filler composition such that, when the lavatory cleaning cake is immersed in an aqueous solution, the quantity of dye released into solution is for a time substantially equivalent to a release of the iodophor into solution from the cake.

The control of residence time of the composition in the dry mixer composition in the turbulizer is by rotor speed and paddle setting.

DESCRIPTION OF THE PREFERRED EMBODIMENT

The invention is a process for manufacturing an iodophor filler for a lavatory cleaning cake. The process involves mixing in a dry-mixer means or "Turbulizer" a dry filler composition. The dry filler composition contains an adsorbent. The dry-mixer means provides a uniform turbulent flow to this dry filler composition as this composition passes through the dry-mixer means. The method then involves wetting the dry filler composition with a liquid iodophor while the composition is in the uniform turbulent flow. Agglomerating of the wetted filler composition then occurs within a controlled residence time of the wetted filler composition in the dry-mixer means. During this residence time, the iodophor is substantially, uniformly distributed throughout the dry filler composition. The dry filler composition, desirably, includes both a dry adsorbent and a dry absorbent. This invention also, includes the product of the process.

Figure 1:
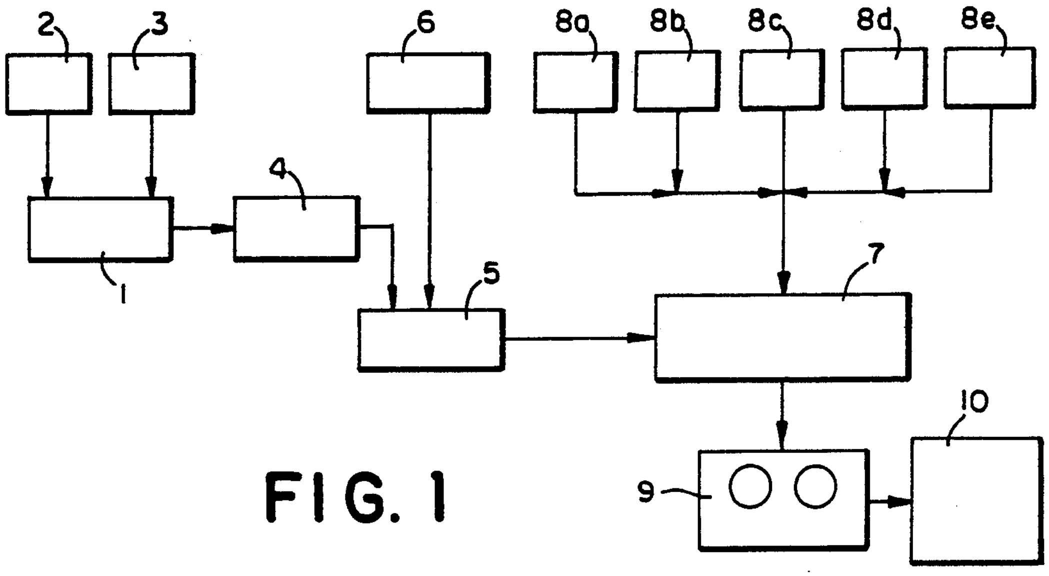
FIG. 1 is a flow diagram of the apparatuses and compositions used in the preferred embodiment of the invention.

FIG. 1 is a flow diagram of the apparatuses and compositions used in the preferred embodiment of the invention. Variations of the depicted equipment, compositions, and the flow diagram can be made within the scope of the present invention.

A first blender 1 receives a dry adsorbent from a first hopper 2 and a dry absorbent from a second hopper 3. The first blender 1 can be any blending means that is capable of mixing dry powder and/or granular compositions together. Such blending means include paddle mixers and worm screw mixers. These blending means are commercially available. The blending means of the preferred embodiment is sold under the trade name, "Nauta mixer".

The blended dry adsorbent and dry absorbent provide a filler composition. The filler composition is propelled or fed through an accurate propelling means 4. The accurate propelling means 4 can be any means that feeds powder and/or particulate compositions at selectively controlled flow rates. Such propelling means are commercially available and can be selected in order to provide flow rates that are compatible with the filler composition being propelled and compatible with other equipment in the system.

The accurate propelling means 4 supplies the blended filler composition to a dry-mixer means 5. The dry-mixer means 5 performs the step of mixing the dry filler composition in a uniform turbulent flow. The dry-mixer means 5 desirably maintains the dry filler composition in a uniform turbulent flow as the dry filler composition passes through a substantial portion or all of an internal chamber of the dry-mixer means 5. Suitable commercial products are available that provide the uniform turbulent flow of dry compositions which is required of the dry-mixer means 5 of this invention. The preferred embodiment of this invention utilizes a dry-mixer means manufactured by the Bepex Corporation under the trade name, "Turbulizer".

An alternate means to combine the dry adsorbent and dry absorbent is to feed each dry component through separate accurate propelling means directly into the inlet of the "Turbulizer". Each accurate propelling means controls the flow rate via a loss-in-weight/master-slave control device.

The filler composition, while it is in turbulent flow within the dry-mixer means 5, undergoes "wetting" with a liquid iodophor from a reservoir dispenser 6. The reservoir dispenser 6 provides the liquid iodophor to the dry-mixer means 5 at a rate of flow which is controlled through the loss-in-weight/master-slave device that coats the surface of the particles of the filler composition without dissolving the particles. A desirable ratio of liquid iodophor to filler composition may range from about 1:50 to 1:10, preferably, about 1:10. This wetting procedure causes the iodophor to be substantially, uniformly distributed throughout the filler composition. The desirable result of uniform distribution of the iodophor throughout the filler composition occurs because the liquid iodophor is injected and mixed into turbulent flow of filler composition as it passes through the dry-mixer means 5. Agitated or suspended particles of filler composition are, thus, coated with liquid iodophor. Particles in laminar flow, by contrast, would not be uniformly wetted with the liquid iodophor. Particles in laminar flow would be exposed and, to an extent, dissolved at the surface of the filler composition mass near the injection port for the liquid iodophor of a mixer means. Substantially, uniformly distributed liquid iodophor in the turbulent flow of filler composition permits agglomerating of the wetted filler composition to rapidly and efficiently occur. This invention can produce agglomerates of filler composition, having substantially, uniformly distributed iodophor within a residence time of the wetted filler composition in the dry-mixer means 5. The term "substantially, uniformly distributed iodophor" is defined within the context of this invention, as meaning that the concentration of iodophor on the surface of random samples of agglomerates is approximately equal.

The agglomerated filler composition exits the dry-mixer means 5 and is passed or transferred to a second blender 7. The second blender 7 can be any blending means that is capable of mixing dry powder and/or granular compositions together. Such blending means include paddle mixers and worm screw mixers. These blending means are commercially available. The blending means of the preferred embodiment is sold under the trade name, "Nauta Mixer".

Additional compositions are supplied to the second blender 7 from at least one hopper 8*a* through 8*e*. The hopper 8*a* supplies dye to the second blender 7. It is desirable that a binder, such as a polyethylene oxide polymer, be supplied to the agglomerated filler composition from a hopper 8*b*. The preferred embodiment of the invention provides optional, but desirable, compositions to the agglomerated filler composition including polyvinyl pyrrolidone Iodine Complex from a hopper 8*c*, polyethylene glycol distearate from a hopper 8*d*, guar gum from a hopper 8*e*, and Polyacrylic Acid Resin from a hopper 8*f*. These additional compositions are supplied to the second blender 7 at a rate that provides a selected quantity of each additional composition in a desired concentration to the agglomerated filler composition. Means for supplying measured rates of additional compositions are known in the art and commercially available.

The blended, dye-containing filler composition exits the second blender 7 and is supplied to a means for compressing particulates 9. The means for compressing particulates 9 is desirably a "roller compactor". Roller compactors are commercially available and operated by compressing particulates, such as powders or agglomerates between two counter rotating rolls. The compressed particulate exits the rollers at a known, selected density in the form of a solid compact or sheet. The density of the compact is sufficient to cause the compressed filler composition to be a solid. Typically, the rollers of a roller compactor are adjusted in order to compress a particular material into a solid block of a desired size.

The solid compressed sheets or blocks exit the means for compressing particulates 9 and enters a mill which grinds the compact into preselected granular form. These granules exit the mill and enter a classifier which selectively separates the granules into undersized granules, oversized granules, and correct sized granules. The correct size granules exit the classifier and enter a tablet press 10. Tablet presses are known in the art and are commercially available. Tablet presses "stamp" the granules of compressed filler composition to provide a solid. The resulting solid is, typically, shaped to be a disk or tablet, but can vary in shape and form. The solid comprised a known quantity of iodophor and dye-containing composition at a known density. The density of the final solid can be selected to provide the solid with desired dissolution characteristics.

Figure 3:
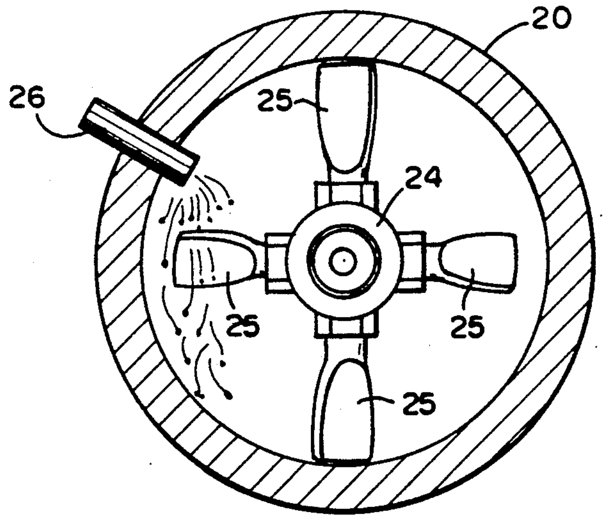
FIG. 3 is a side cutaway view of the rotor assembly inside the cylindrical casing of the dry-mixer means.
Figure 2:
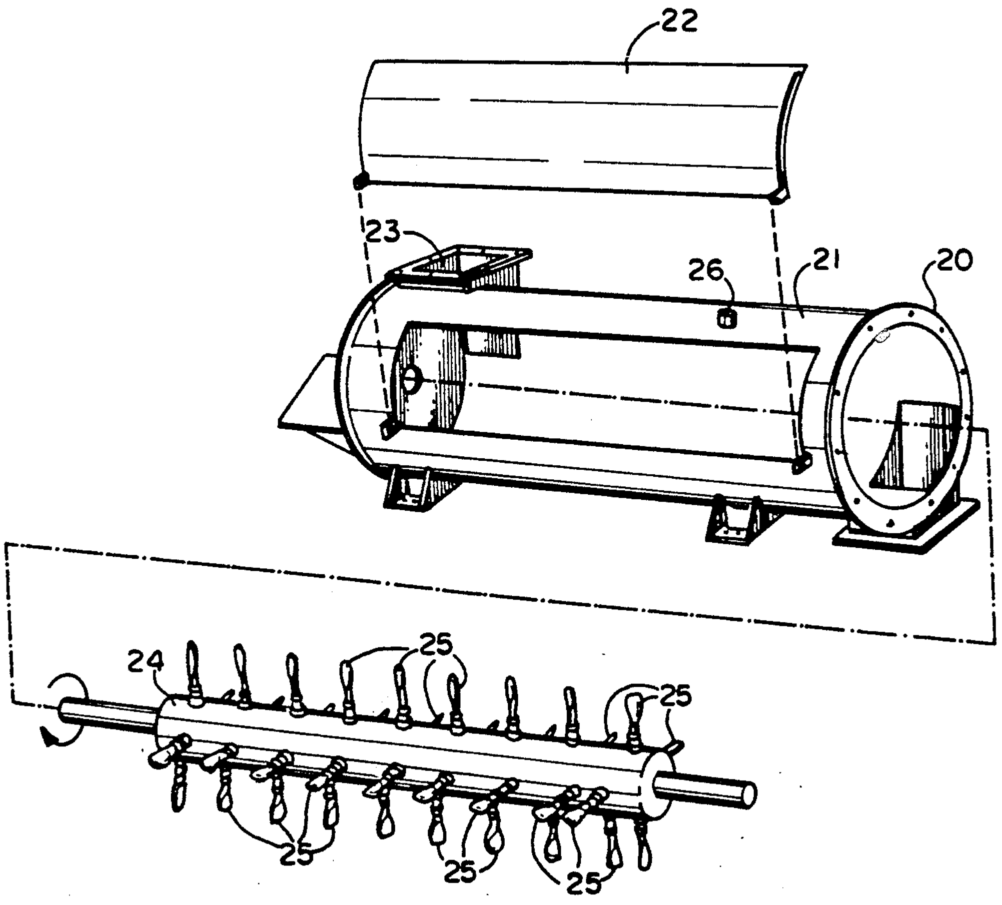
FIG. 2 is a perspective view of a dry-mixer means.

FIG. 2 illustrates a perspective view of a dry-mixer means of the preferred embodiment of this invention. The dry-mixer means of this figure is a 20 inch long "jacketed model" of a Turbulizer 20 that is manufactured by the Bepex Corporation. The Turbulizer 20 of this embodiment has a steel cylindrical casing 21 with an access cover 22. An inlet port 23 receives dry filler composition. The rotor assembly 24 is mounted axially within the cylindrical casing 21 by appropriate means including balancing disks and bearings (not shown). The rotor assembly 24 is rotated by a motor (not shown) and the speed of rotation can be selected or controlled, as appropriate, by means known in the art. The rotor assembly 24 has a plurality of variably pitched paddles 25. The variable pitch paddles 25 can be set at angles to the axis of rotation. The selection of an angle of a blade determines whether that blade (1) propels filler composition through the cylindrical casing 21, (2) creates a back flow and turbulence of the filler composition in the cylindrical casing 21, or (3) mixes the filler composition without axially propelling the filler composition in either direction through the cylindrical casing 21. The gap between the paddle tip and casing can also be adjusted to control the amount of shear applied to the cylindrical casing 21. agglomerate. A liquid inlet port 26 is positioned on the FIG. 3 is a side cutaway view of the rotor assembly 24 inside the cylindrical casing 21 of the Turbulizer 20. This figure illustrates the position of the paddles 25 on the rotor assembly 24 within the cylindrical casing 21. Also, illustrated is the liquid injection port 26 on the wall of the cylindrical casing 21.

Figure 4:
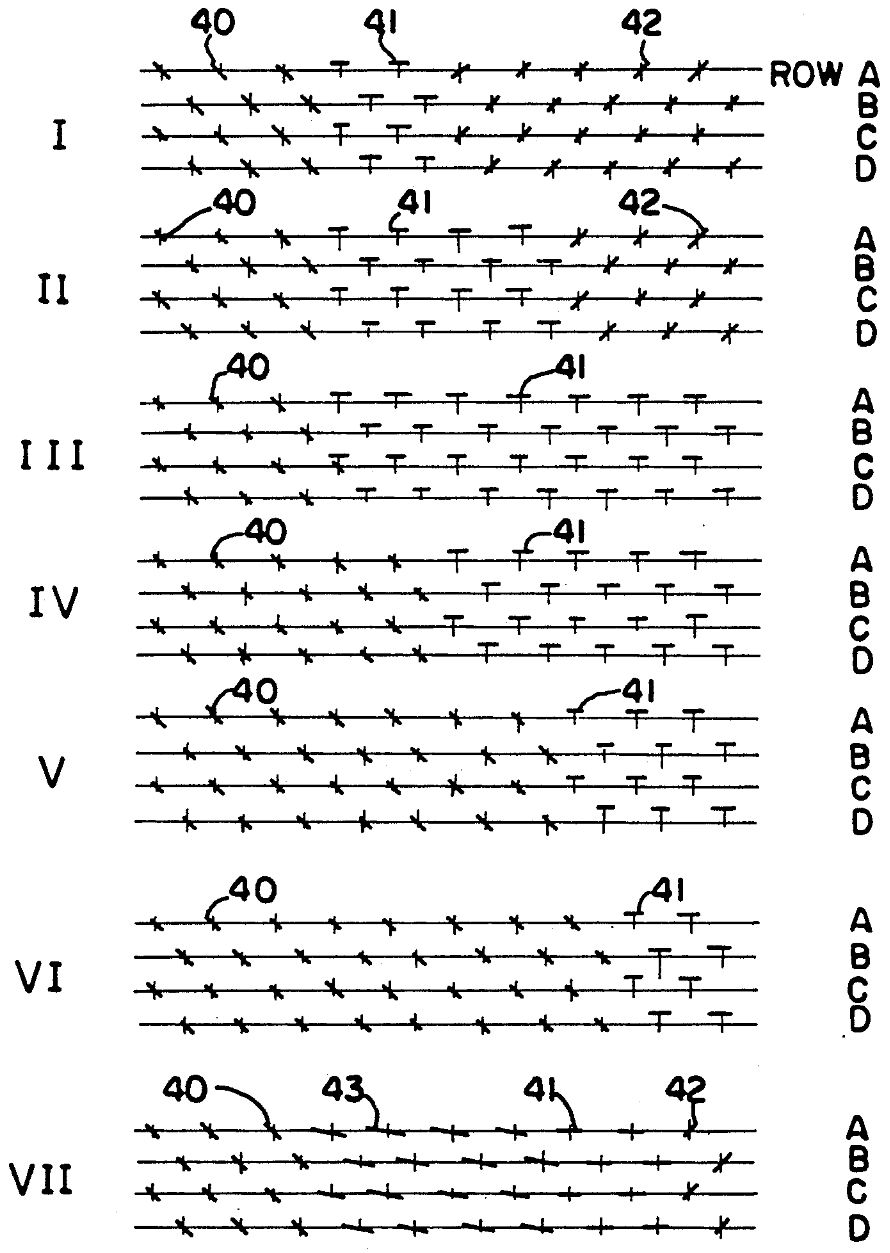
FIG. 4 is a variety of pitch schemes for the paddles of a dry mixer means.

FIG. 4 illustrates seven different pitch schemes for the paddles of a dry-mixer means. Each rotor assembly in this dry-mixer means of the preferred embodiment of this invention has four rows of paddles A, B, C, and D with twenty "columns" of paddles with two paddles in each column. The two paddles in each column are opposite one another and share a central axis that is perpendicular to the axis of rotation of the rotor assembly.

The seven schemes of FIG. 4 are as follows. The degrees of pitch are determined by the angle between the face of a paddle and the axis of rotation of the rotor assembly. The first paddles receive the dry filler composition as it enters the Turbulizer 20 through the inlet port 23 as illustrated in FIG. 2. Pitch scheme I has a paddle combination of 30 percent of 45° forward pitch paddles 40, 20 percent of 0° pitch paddles 41, and 50 percent of 45° backward pitch paddles 42. Pitch scheme II has a paddle combination of 30 percent of 45° forward pitch paddles 40, 40 percent of 0° pitch paddles 41, and 30 percent of 45° backward pitch paddles 42. Pitch scheme III has a paddle combination of 30 percent of 45° forward pitch paddles 40, and 70 percent of 0° pitch paddles 41. Pitch scheme IV has a paddle combination of 50 percent of 45° forward pitch paddles 40, and 50 percent of 0° pitch paddles 41. Pitch scheme V has a paddle combination of 70 percent 45° forward pitch paddles 40, and 30 percent of 0° pitch paddles 41. Pitch scheme VI has a paddle combination of 80 percent of 45° forward pitch paddles 40, and 20 percent of 0° pitch paddles 41. Pitch scheme VII has a paddle combination of 30 percent 45° forward pitch paddles 40, 40 percent 15° forward pitch paddles 43, 20 percent 0° pitch paddles 41, and 10 percent 45° backward pitch paddles 42. Other pitch schemes and angles of pitch can be used with this invention.

Desirable embodiments of the invention provide a solid cake composition which comprises an iodophor, a polyethylene oxide polymer having a molecular weight from about 1 to about 6 million, a dye, calcium sulfate, and optional ingredients selected from the groups consisting of fragrances, binders, filler material and mixtures thereof.

The type of iodophor utilized is not critical to the present invention, but the amount of iodophor used must contain an amount of iodine calculated as elemental iodine to comprise about at least 1 percent and, preferably, between about 1 and about 6 percent by weight of composition. A greater amount of iodine can be utilized, but is not necessary for achieving the objects of the invention. A particularly desirable cake composition has a ratio of iodophor, calculated as elemental iodine, to dye of about 2.5:10 and, preferably, 3.5:5 so as to result in a life of the iodophor in the cake composition of substantially the same as the life of the dye in the cake composition. It is understood that a greater amount of iodophor can be present. However, a suitable commercial product having an "in-tank life" of about 30 days needs only up to about 6 percent of iodophor calculated as elemental iodine. The greater amount only increases the cost of the cleansing block. The use of up to about 5 percent by weight of composition of citric acid, tartaric acid or a free acid form of a phosphonate compound produces a greater intensification of the sanitizing effect of the iodophor.

Calcium sulfate is desirably utilized in this invention as an adsorbent in either the dihydrate or anhydrous form. Preferably, the two forms are utilized together. When only the dihydrate form is utilized, it is advantageous that the polyethylene oxide polymer be present in an amount of at least 2.0 percent. Calcium sulfate serves both as an adsorbing agent for the iodophor and a determinant for controlling solubility of the resulting solid or toilet cake.

A desirable embodiment of the invention includes a toilet cake composition in tablet form having an in-tank life of about 30 days. This toilet cake comprises an amount of iodophor containing an amount of iodine calculated as elemental iodine to comprise preferably about 1 to 6 percent by weight of composition. About 2 to 20 percent by weight of composition, and preferably, about 2 to 5 percent by weight of the composition is a polyethylene oxide homopolymer having a molecular weight of between about 1 to 6 million. About 1 to 75 percent by weight of the composition is calcium sulfate, about 1 to 10 percent by weight of the composition is dye, and the remainder of the ingredients optionally comprise ingredients from the group consisting of surfactants, fragrances, fillers, binders, extenders and the like.

A suitable composition for forming a tablet by the compression method comprises an amount of iodophor-containing an amount of iodine calculated as elemental iodine to comprise about 1 to 6 percent by weight of composition, about 40 to 60 percent by weight of calcium sulfate dihydrate, about 2.0 to 30 percent by weight calcium sulfate anhydrous, about 2 to 5 percent by weight polyethylene oxide homopolymer having a molecular weight between 1 and 6 million, preferably as a mixture of high and low molecular weights, about 1 to 20 percent by weight binder, about 2 to 10 percent by weight fillers including optionally, plasticizers, fragrances, and perfumes. It is also advantageous to include up to about 5.0 percent by weight of a flow control agent and/or absorber for powders, for example, fumed silica.

Suitable binders, which can be utilized with this invention, include ethylene oxide/propylene oxide copolymers, guar gum, polyvinyl pyrrolidone, hydroxyethylene cellulose, PEG 8000, polyethylene glycol distearate, pdyacrylic acid resins, and the like.

Tablets, which are to be prepared by extrusion, desirably contain about 10 to 25 percent by weight of extrusion aids, for example, anionic alkylates such as sodium dodecylbenzene sulfonate.

Preferably, the amount of iodophor placed in the composition is chosen so as to last at least as long or "through at least as many flushes" as the amount of dye composition in the dye composition dispensing means. When the consumer no longer sees any color appear in the bowl after flushing the toilet, the lack of color indicates that it is time to replace the system containing the dye and sanitizer. It is desirable to have a persistent color in the toilet bowl between flushes and, therefore, it is preferable that the supply of sanitizer last for at least as long as the supply of dye.

Various optional materials can be included in the compositions herein.

Dyes can be included at levels of from about 1.0 to 10.0 percent by weight. Examples of suitable dyes are Alizarine Light Blue B (C.I. 63010), Carta Blue VP (C.I. 24401), Acid Green 2G (C.I. 42085), Astragon Green D (C.I. 42040), Supranol Cyanine 7B (C.I. 42675), Maxilon Blue 3RL (C.I. Basic Blue 80), Acid Yellow 23, Acid Violet 17, a direct violet dye (Direct Violet 51), Drimarine Blue Z-RL (C.I. Reactive Blue 18), Alizarine Light Blue H-RL (C.I. Acid Blue 182), FD&C Blue No. 1, FD&C Green No. 3 and Acid Blue No. 9. Others are disclosed in the aforementioned U.S. Pat. Nos. 4,310,434 and 4,477,363, which are herein incorporated by reference.

The cakes can also contain perfumes to impart an acceptable odor to the flushing water. The perfume can be in solid form and is suitably present in an amount up to 10 percent by weight. In this connection, it can be noted that the term "perfume" is intended to refer to any material giving an acceptable odor and thus materials giving a "disinfectant" odor such as essential oils, pine extracts, terpenes, ortho phenyl phenol or paradichlorobenzene can be employed. The essential oils and pine extracts also contribute as plasticizers and are functional to a degree in extending block life. Other suitable perfumes or fragrances are disclosed in U.S. Pat. No. 4,396,522 to Callicott, et al., which is herein incorporated by reference.

The cake formulation can also contain other binding, anti-adhesion and/or plasticizing ingredients serving to assist in the manufacture thereof, for example, polypropylene glycol having a molecular weight from about 300 to about 10,000 in an amount up to about 20 percent by weight and preferably about 4 percent to about 15 percent by weight of the mixture can be used.

If desired, other halophors can be added, for example, bromophors such as dibromopropamidine isothionate (sold under the trademark BRULIDINE), 2-bromo-2-nitropropane-1, 3-diol (sold under the trademark BRONOPOL), bromochlorodimethyl hydantoin, dibromodimethyl hydantoin, and 2-cyano-2,2-dibromo acetamide, preferably in an amount up to about 5 percent by weight.

In order that the invention may be better understood the following examples are given by way of illustration only.

In the examples, all parts and percentages are by weight of composition unless otherwise stated.

The following examples are for compositions and procedures suited for providing shaped bodies of blocks of the invention. Examples 1 through 4 represent desirable embodiments of the composition of the invention. Examples 5 through 15 represent desirable embodiments of the process of the invention.

EXAMPLE 1

A solid compacted sanitizing composition cake was prepared by dry-mixing the following ingredients and then subjecting the mixture to a compaction pressure of about 3.6–10.8 tons per square inch on a Manesty RS3 Tablet Press. The ingredients and concentrations of this example are presented with trade names in parentheses, in Table 1 as follows.

TABLE 1

| Ingredient | Percent |
|---|---|
| Calcium Sulfate Dihydrate (fine) | 63.95 |
| Calcium Sulfate Anhydrous (fine) | 10.00 |
| Fumed Silica | 5.00 |
| Iodophor (Biopal NR-20) | 9.75 |
| Polyvinyl Pyrrolidone Iodine Complex (Povidone) | 4.30 |
| Dye (Acid Blue #9) | 5.00 |
| Polyethylene oxide polymer (Polyox 60K) | 2.00 |

The resulting tablet of this example had an in-tank life of about 30 days and met the EPA dye and iodophor dissolution requirements until the end of the period or life of the toilet cake.

EXAMPLE 2

A cleansing block is formed with the following composition and the procedure of Example 1. The ingredients and concentrations of this example are presented in Table 2 as follows.

The resulting tablet of this example had an in-tank life of about 30 days and met the EPA dye and iodophor dissolution requirements until the end of the period or life of the toilet cake which is about 33 days. If desired, in place of a portion of the calcium sulfate there can be added a fragrance to this composition.

EXAMPLE 3

A cleansing block is formed with the following composition and the procedure of Example 1. The ingredients and concentrations of this example are presented in Table 3 as follows.

TABLE 3

| Ingredient | Percent |
|---|---|
| Calcium Sulfate Fine Dihydrate (fine) | 48.0 |
| Calcium Sulfate Fine Anhydrous (fine) | 24.8 |
| Fumed Silica | 5.0 |
| Cleanfront (liquid iodophor) | 10.5 |
| Povidone | 6.7 |
| Acid Blue #9 | 5.0 |
| | 100.0 |

The resulting tablet of this example had an in-tank life of about 30 days and met the EPA dye and iodophor dissolution requirements until the end of the period or life of the toilet cake. If desired, in place of a portion of the calcium sulfate, there can be added fragrances and citric acid to this composition.

EXAMPLE 4

A cleansing block is prepared from the following composition and the procedure of Example 1. The ingredients and concentrations of this example are presented in Table 4 as follows.

TABLE 4

| Ingredient | Percent |
|---|---|
| Calcium Sulfate, dihydrate | 49.35 |
| Aerosil 380 | 1.75 |
| Cleanfront | 5.00 |
| PVP-I2 | 13.90 |
| Acid Blue #9 | 5.00 |
| Polyethylene oxide polymer | 2.00 |
| Polyethylene Glycol Distearate | 10.00 |
| Guar Gum | 12.50 |
| Polyacrylic Acid Resin | 0.50 |
| | 100.00 |

The formula provides a cleansing block having good anti-bacterial properties and complies with the EPA dissolution requirements.

In lieu of sodium dodecyl benzene sulfonate there can be utilized in its place a similar amount of sodium alpha olefin ($C_{14}$–$C_{16}$) sulfonate or oleyl/palmitic succinate amide, peg 6000 distearate, or the like.

EXAMPLE 5

Example 5 demonstrates the process of this invention for manufacturing a cleansing block. The composition of Example 4 provides the ingredients and their concentrations for this example.

The agglomeration procedure of this example uses a model TCS-8 Turbulizer manufactured by the Strong-Scott Manufacturing Company equipped with a 10 horse power motor. The Turbulizer rotor assembly is fitted with a variable speed rotor having 40 adjustable paddles which are provided by the manufacturer. The dry filler composition feed is controlled by a feed screw attached to a small hopper. The liquid iodophor is pumped through a ⅜ inch tube by a Viking positive displacement pump, into the top of the Turbulizer at the "first" port which is provided on such machines by the manufacturer. The solid to liquid ratio of this example is calibrated to provide 415 pounds of solid to 85 pounds of liquid. The paddle positions are set for maximum residence time as illustrated in paddle scheme I of FIG. 4. Other parameters used in this example are presented in Table 5 as follows.

TABLE 5

| Parameter | Exp 5 | Value |
|---|---|---|
| Paddle Scheme | I | FIG. 4 |
| Rotor Speed | 2600 | RPM |
| Solid Feed Rate | 415 | LBS/HR |
| Liquid Feed Rate | 85 | LBS/HR |
| Main Rotor Amp | 20 | KW-HR |
| Temperature/Solid Feed | 68° | F. |
| Temperature/Liquid Feed | 68° | F. |
| Agglomerate Exit Temp. | 90° | F. |

This example produces a dark brown wet product with some build up on the Turbulizer interior cylinder wall. The build up of agglomerate on the cylinder wall causes overloading of the Turbulizer. The agglomerate produced by this example requires further drying before being compressed. Adjustment of rotor speed and residence time avoids the build up.

EXAMPLES 6 THROUGH 10

Examples 6 through 10 demonstrate desirable embodiments of this invention for manufacturing a cleansing block. The composition and procedures for these examples are the same as for Example 5 except that residence times and rotor speeds are incrementally decreased until a non-uniform, light tan dusty, free-flowing powdered agglomerate is obtained. Other parameters of these examples are presented in Table 6 as follows.

TABLE 6

| Parameters | Exp 7 | Exp 8 | Exp 9 | Exp 10 | Value |
|---|---|---|---|---|---|
| Paddle Scheme | II | III | IV | V | FIG. 4 |
| Rotor Speed | 2600 | 2600 | 1978 | 1978 | RPM |
| Solid Feed Rate | 415 | 415 | 415 | 415 | LBS/HR |
| Liquid Feed Rate | 85 | 85 | 85 | 85 | LBS/HR |
| Main Rotor Amp | 20 | 20 | 15 | 6 | KW-HR |
| Temp/Solid Feed | 68° | 68° | 68° | 68° | F. |
| Temp/Liquid Feed | 68° | 68° | 68° | 68° | F. |
| Agglom. Exit Temp | 90° | 90° | 90° | 90° | F. |

The paddle settings and rotor speeds of these examples incrementally imposed the characteristics of the agglomerate produced by each example. (The agglomerates produced by Examples 7 and 8 had a higher concentration of wetness than the agglomerates produced by Examples 9 and 10.) A high concentration of wet particles in an agglomerate requires additional procedures before the agglomerate is compressed and stamped into a solid.

EXAMPLES 11 THROUGH 13

Examples 11 through 13 demonstrate very desirable embodiments of this invention for manufacturing a cleansing block. The composition and procedures for these examples are the same as for Example 5 except that residence times and rotor speeds are altered to produce a uniform, light tan dusty, free-flowing powdered agglomerate. Other parameters of these examples are presented in Table 7 as follows.

TABLE 7

| Parameters | Exp 11 | Exp 12 | Exp 13 | Value |
|---|---|---|---|---|
| Paddle Scheme | VI | VI | VI | FIG. 4 |
| Rotor Speed | 1978 | 2885 | 3115 | RPM |
| Solid Feed Rate | 415 | 415 | 415 | LBS/HR |
| Liquid Feed Rate | 85 | 85 | 85 | LBS/HR |
| Main Rotor Amp | 6 | 7.5 | 7.5 | KW-HR |
| Temp/Solid Feed | 68° | 68° | 68° | F. |
| Temp/Liquid Feed | 68° | 68° | 68° | F. |
| Agglom. Exit Temp | 80° | 78° | 78° | F. |

The paddle settings and rotor speeds of these examples further improved the characteristics of the agglomerates. The agglomerates of these examples are blended with other ingredients then immediately compressed into a solid block and stamped into tablet shaped forms. The agglomerates of Example 13 provides the most desirable characteristics. Example 13 represents the preferred embodiment and best mode of the invention. The resulting toilet cleansing blocks of these examples release both iodophor and dye for substantially the same duration of time once immersed in water.

EXAMPLE 14

Example 14 demonstrates an alternative embodiment of the invention for manufacturing a cleansing block. The composition and procedures for this example are the same as for Example 5 except that (1) the composition is altered to include 9.75 percent Biopal, 4.3 percent PVP-I2, and 5 percent Aerosil and (2) residence times and rotor speeds as presented in Table 8.

TABLE 8

| Parameters | Exp 14 | Value |
|---|---|---|
| Paddle Scheme | VI | FIG. 4 |
| Rotor Speed | 3115 | RPM |
| Solid Feed Rate | 450 | LBS/HR |
| Liquid Feed Rate | 55 | LBS/HR |
| Main Rotor Amp | 7.5 | KW-HR |
| Temp/Solid Feed | 68° | F. |
| Temp/Liquid Feed | 68° | F. |
| Agglomerate Exit Temp | 78° | F. |

The uniform agglomerate of this example is blended with other ingredients then compressed into a solid block and stamped into tablet shaped forms. The resulting toilet cleansing blocks of this example release both iodophor and dye for substantially the same duration of time once immersed in water.

EXAMPLE 15

Example 15 demonstrates an alternative embodiment of the invention for manufacturing a cleansing block. The composition and procedures for this example are the same as for Example 5 except that residence times and rotor speeds are altered as presented in Table 9. This example uses a solid material feeder to the Turbulizer, that is sold under the trade name, "AccuRate", and a liquid material feeder to the Turbulizer, that is sold under the trade name, "Masterflex".

TABLE 9

| Parameters | Exp 15 | Value |
|---|---|---|
| Paddle Scheme | VII | FIG. 4 |
| Rotor Speed | 2040 | RPM |
| Solid Feed Rate | 200 | LBS/HR |
| Liquid Feed Rate | 23.5 | LBS/HR |
| Main Rotor Amp | 10 | KW-HR |
| Temp/Solid Feed | 68° | F. |
| Temp/Liquid Feed | 68° | F. |
| Agglom. Exit Temp | 78° | F. |

The uniform agglomerate of this example is blended with other ingredients then compressed into a solid block and stamped into tablet shaped forms. The resulting toilet cleansing blocks of this example release both iodophor and dye for substantially the same duration of time once immersed in water.

The principals, preferred embodiments, and modes of operation of the present invention have been described in the foregoing specification. The invention which is intended to be protected herein, however, is not to be construed as limited to particular forms disclosed, since these are to be regarded as illustrative rather than restrictive. Variations and changes can be made by those skilled in the art without departing from the spirit of the invention.

What is claimed is:

1. A process for manufacturing an iodophor filler for a lavatory cleaning cake comprising:

mixing in a dry-mixer means comprising a first and second set of blades a dry filler composition, said dry filler composition comprising an adsorbent comprising calcium sulfate and an absorbent comprising silica, said first set of blades homogeneously mixing said dry filler composition and then propelling said dry filler composition into said second set of blades, whereby said dry-mixer means provides a uniform turbulent flow of said dry filler composition through said dry-mixer means;

wetting said dry filler composition in said uniform turbulent flow with a liquid iodophor whereby said iodophor is substantially, uniformly distributed throughout said filler composition; and agglomerating said wetted filler composition within a controlled residence time of said wetted filler composition in said dry-mixer means.

2. The process of claim 1 wherein the ratio of liquid iodophor to filler composition is about 1:50 to 1:10.

3. A process for manufacturing an iodophor filler for a lavatory cleaning cake comprising:

blending a dry adsorbent comprising calcium sulfate and a dry absorbent comprising silica to produce a filler composition;

mixing said filler composition in a dry-mixer means, comprising a first and second set of blades, said dry mixer means providing a uniform turbulent flow of said filler composition through said dry-mixer means;

wetting said filler composition during said uniform turbulent flow with a liquid iodophor whereby said iodophor is substantially, uniformly distributed throughout said filler composition; and agglomerating said wetted filler composition within a controlled residence time of said wetted filler composition in said dry-mixer.

4. The process of claim 3, wherein said dry-mixer means contains a rotor having a first set and a second set of paddle means, and including the step of axially positioning said first set of said paddle means on said rotor to receive said dry filler composition upon entry of said dry filler composition into said dry-mixer means and then selectively angularly positioning said first set of pad means to both homogeneously mix said dry filler composition and propel said dry filler composition into said second set of paddle means.

5. The process of claim 4, including the step of axially positioning said second set of said paddle means on said rotor to receive said liquid iodophor upon entry of said liquid iodophor into said dry-mixer means and maintaining said turbulent flow of said dry filler composition being propelled through said dry-mixer means.

6. The process of claim 3 wherein the ratio of liquid iodophor to filler composition is about 1:50 to 1:10.

7. The process of claim 3, wherein said blending of said dry adsorbent and said dry absorbent to form a dry filler composition is performed by a blender, said process further comprising a step of feeding said blended filler composition to said dry-mixer means.

8. A process for manufacturing an iodophor lavatory cleaning cake comprising:

mixing in a dry-mixer means a dry filler composition, said dry filler composition containing an adsorbent comprising calcium sulfate and an absorbent comprising silica, said dry-mixer means providing a uniform turbulent flow of said dry filler composition through said dry-mixer means;

wetting said dry filler composition in said uniform turbulent flow with a liquid iodophor whereby said iodophor is substantially, uniformly distributed throughout said filler composition;

agglomerating said wetted filler composition within a controlled residence time of said wetted filler composition in said dry-mixer means;

blending a sufficient quantity of a dye into said agglomerated filler composition; and compacting said dye-containing agglomerated filler composition into a solid form whereby, when said solid form is immersed in an aqueous solution, said sufficient quantity of said dye releases into solution for a time substantially equivalent to a release of said iodophor into solution from said form.

9. The process of claim 8 wherein the ratio of liquid iodophor to filler composition is about 1:50 to 1:10.

10. The process of claim 8, wherein said blending of said dye into said agglomerated filler composition includes blending with at least one binder.

11. The process of claim 10, wherein said binder is a member of the group consisting of polyethylene oxide polymer, ethylene oxide/propylene oxide copolymer, guar gum, polyvinyl pyrrolidone, hydroxyethyl cellulose, polyethylene glycol, and polyethylene glycol distearate.

12. The process of claim 10, wherein said blending of said dye into said agglomerated filler composition includes blending with an additional iodophor, polyvinyl pyrrolidone iodine complex.

13. The process of claim 8, wherein said dry-mixer means has a rotor having a first set and a second set of said paddle means, and including the step of axially positioning said first set of said paddle means on said rotor to receive said dry filler composition upon entry of said dry filler composition into said chamber and selectively angularly positioning said first set of paddle means on said rotor to both homogeneously mix said dry filler composition and propel said dry filler composition into said second set of paddle means.

14. The process of claim 8, including the step of axially positioning said second set of said paddle means on said rotor to receive said liquid iodophor upon entry of said liquid into said dry-mixer means and maintaining said turbulent flow of said dry filler composition being propelled through said dry-mixer means.

15. The process of claim 8, wherein said blending of said dry adsorbent and said dry absorbent to form a dry filler composition is performed by a blender, said process further comprising the step of feeding said blended filler composition to said dry-mixer means.

16. A process for manufacturing an iodophor lavatory cleaning cake comprising:

blending a dry adsorbent comprising calcium sulfate and a dry absorbent comprising formed silica to produce a filler composition;

mixing said filler composition in a dry-mixer means, said dry-mixer means providing a uniform turbulent flow of said filler composition through said dry-mixer means;

wetting said dry filler composition in said uniform turbulent flow with a liquid iodophor whereby said iodophor is substantially, uniformly distributed throughout said filler composition;

agglomerating said wetted filler composition within a controlled residence time of said wetted filler composition in said dry-mixer means;

blending a sufficient quantity of a dye into said agglomerated filler composition;

compressing said dye-containing filler composition into a solid; and stamping said compressed filler composition into a solid form whereby, when said solid form is immersed in an aqueous solution, said sufficient quantity of said dye releases into solution for a time substantially equivalent to a release of said iodophor into solution from said solid form.

17. The process of claim 16, wherein said blending of said dye into said agglomerated filler composition includes blending with at least one binder.

18. The process of claim 17, wherein said binder is a member of the group consisting of polyethylene oxide polymer, ethylene oxide/propylene oxide copolymer, guar gum, polyvinyl pyrrolidone, hydroxyethyl cellulose, polyethylene glycol, and polyethylene glycol distearate.

19. The process of claim 16, wherein said blending of said dye into said agglomerated filler composition includes blending with an additional iodophor, polyvinyl pyrrolidone iodine complex.

20. The process of claim 16, wherein said dry-mixer means contains a rotor having a first set and a second set of said paddle means, and including the step of axially positioning said first set of said paddle means on said rotor to receive said dry filler composition upon entry of said dry filler composition into said chamber and selectively angularly positioning said first set of paddle means on said rotor to both homogeneously mix said dry filler composition and propel said dry filler composition into said second set of paddle means.

21. The process claim of 20, including the step of axially positioning said second set of said paddle means on said rotor to receive said liquid iodophor upon entry of said liquid iodophor into said chamber and maintaining said turbulent flow of said dry filler composition being propelled through said chamber.

22. The process of claim 16, wherein said blending of said dry adsorbent and said dry absorbent to form a dry filler composition is performed by a blender, said process further comprising the step of feeding said blended filler composition to said dry-mixer means.

23. The process of claim 16, comprising compressing said dye-containing agglomerated filler composition with a roller compactor into a solid form.

24. The process of claim 16, comprising stamping said compressed filler composition by a tablet press.

25. The process of claim 16, wherein said dry adsorbent is a member of the group consisting of calcium sulfate dihydrate, anhydrous calcium sulfate, and mixtures thereof.

26. The process of claim 16, wherein said absorbent is fumed silica.

27. The process of claim 16 wherein the ratio of liquid iodophor to filler composition is about 1:50 to 1:10.

28. A process for manufacturing an iodophor lavatory cleaning cake comprising:

blending between about 1 percent and about 75 percent by weight of cleansing block composition of calcium sulfate and between about 0 percent and 5 percent by weight of cleansing block composition of fumed silica to produce a filler composition;

mixing said filler composition in a dry-mixer means, said dry-mixer means providing a uniform turbulent flow of said filler composition though said dry-mixer means;

wetting said dry filler composition in said uniform turbulent flow with an amount of liquid iodophor containing iodine calculated as elemental iodine to comprise at least about 1 percent by weight of cleansing block composition whereby said iodophor is substantially, uniformly distributed throughout said filler composition;

agglomerating said wetted filler composition within a controlled residence time of said wetted filler composition in said dry-mixer means;

blending into said agglomerated filler composition (1) between about 1 percent and about 10 percent by weight of cleansing block composition of dye, (2) between about 2 percent and 20 percent by weight of cleansing block composition of polyethylene oxide polymer, and (3) the remainder being optional ingredients selected from the group consisting of fragrances, binders, filler material, and mixtures thereof;

compressing said dye-containing filler composition into a solid; and stamping said compressed filler composition into a solid form whereby, when said solid form is immersed in an aqueous solution, said sufficient quantity of said dye releases into solution for a time substantially equivalent to a release of said iodophor into solution from said solid form.

* * * * *